United States Patent
Rosney et al.

(10) Patent No.: US 7,214,185 B1
(45) Date of Patent: May 8, 2007

(54) SURGICAL ACCESS DEVICE

(75) Inventors: Damien Rosney, County Offaly (IE);
Christy Cummins, County Offaly (IE);
Donal Bermingham, County Offaly (IE)

(73) Assignee: Maclachlan & Donaldson, Dublin (IE)

( * ) Notice: Subject to any disclaimer, the term of this patent is extended or adjusted under 35 U.S.C. 154(b) by 0 days.

(21) Appl. No.: 09/936,840

(22) PCT Filed: Mar. 20, 2000

(86) PCT No.: PCT/IE00/00034

§ 371 (c)(1),
(2), (4) Date: Jan. 7, 2002

(87) PCT Pub. No.: WO00/54677

PCT Pub. Date: Sep. 21, 2000

(30) Foreign Application Priority Data

Mar. 18, 1999 (IE) .................................. S990218

(51) Int. Cl.
*A61B 19/00* (2006.01)

(52) U.S. Cl. .................. 600/208; 604/167.01; 606/213

(58) Field of Classification Search ................ 606/108, 606/201, 202, 213, 191, 192; 604/167, 174, 604/256, 523, 237; 600/207, 208, 235
See application file for complete search history.

(56) References Cited

U.S. PATENT DOCUMENTS

| | | | |
|---|---|---|---|
| 1,157,202 A | 10/1915 | Bates et al. | |
| 3,347,227 A | 10/1967 | Harrower | |
| 4,984,564 A | 1/1991 | Yuen | |
| 5,082,005 A * | 1/1992 | Kaldany ..................... | 128/850 |
| 5,159,921 A | 11/1992 | Hoover | |
| 5,213,114 A | 5/1993 | Bailey, Jr. | |
| 5,366,478 A * | 11/1994 | Brinkerhoff et al. ........ | 606/213 |
| 5,514,133 A | 5/1996 | Golub et al. | |
| 5,522,791 A | 6/1996 | Leyva | |
| 5,524,644 A | 6/1996 | Crook | |
| 5,545,179 A | 8/1996 | Williamson, IV | |
| 5,634,911 A * | 6/1997 | Hermann et al. ........... | 604/256 |
| 5,634,937 A * | 6/1997 | Mollenauer et al. ........ | 606/213 |
| 5,636,645 A * | 6/1997 | Ou ............................. | 128/898 |
| 5,640,977 A | 6/1997 | Leahy et al. | |
| 5,649,550 A | 7/1997 | Crook | |
| 5,810,721 A | 9/1998 | Mueller et al. | |
| 5,871,474 A | 2/1999 | Hermann et al. | |

(Continued)

FOREIGN PATENT DOCUMENTS

GB          2275420      *  8/1994      ................. 606/108

(Continued)

*Primary Examiner*—Michael J. Hayes
*Assistant Examiner*—Victor Nguyen
(74) *Attorney, Agent, or Firm*—Tim L. Brackett, Jr.; Nixon Peabody LLP

(57) ABSTRACT

A surgical device for use in minimally invasive surgery in which body cavity is accessed by a surgeon though an access port defined by the device, the device including a body cavity engagement feature for insertion into the incision to locate the device in position, fixing feature with a ring that attaches the device to the patient's skin, and a toroid cell having a bladder filled with a liquid or a gel to prevent substantial leakage of gas from the body cavity and formed to mould about a substantial portion of a surgeon's hand or surgical instrument on insertion.

1 Claim, 2 Drawing Sheets

U.S. PATENT DOCUMENTS

| | | | |
|---|---|---|---|
| 5,906,577 A * | 5/1999 | Beane et al. | 600/207 |
| 5,989,232 A * | 11/1999 | Yoon | 604/523 |
| 6,033,426 A | 3/2000 | Kaji | |
| 6,033,428 A | 3/2000 | Sardella | |
| 6,077,288 A | 6/2000 | Shimomura et al. | |
| 6,142,935 A | 11/2000 | Flom et al. | |
| 6,149,642 A | 11/2000 | Gerhart et al. | |
| 6,254,533 B1 | 7/2001 | Fadem et al. | |
| 6,254,534 B1 | 7/2001 | Butler et al. | |
| 6,276,661 B1 | 8/2001 | Laird | |
| 6,382,211 B1 | 5/2002 | Crook | |
| 6,440,063 B1 | 8/2002 | Beane et al. | |
| 6,450,983 B1 | 9/2002 | Rambo | |
| 2001/0037053 A1 | 11/2001 | Bonadio et al. | |

FOREIGN PATENT DOCUMENTS

| | | | | |
|---|---|---|---|---|
| WO | WO 95/07056 | * | 3/1995 | 606/108 |
| WO | WO 99/25268 | | 5/1999 | |
| WO | WO 00/32120 A1 | | 6/2000 | |
| WO | WO 00/35356 A1 | | 6/2000 | |
| WO | WO 01/08581 A2 | | 2/2001 | |
| WO | WO 01/26559 A1 | | 4/2001 | |
| WO | WO 02/34108 A2 | | 5/2002 | |

* cited by examiner

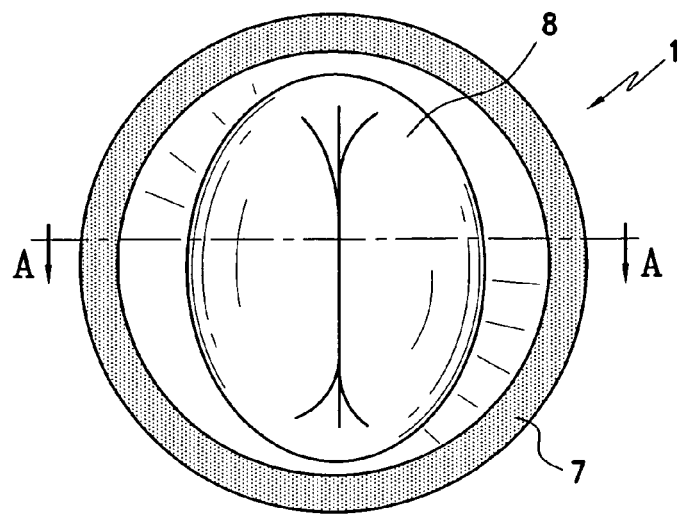
FIG. 1
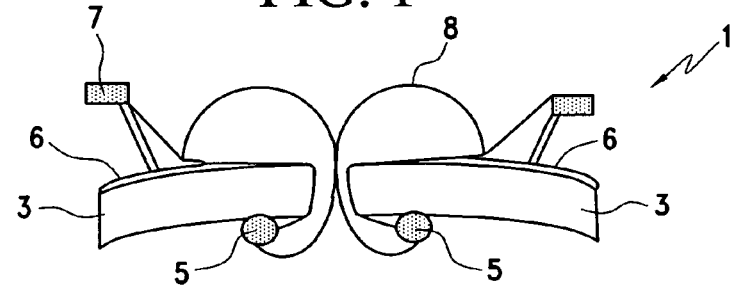
FIG. 2
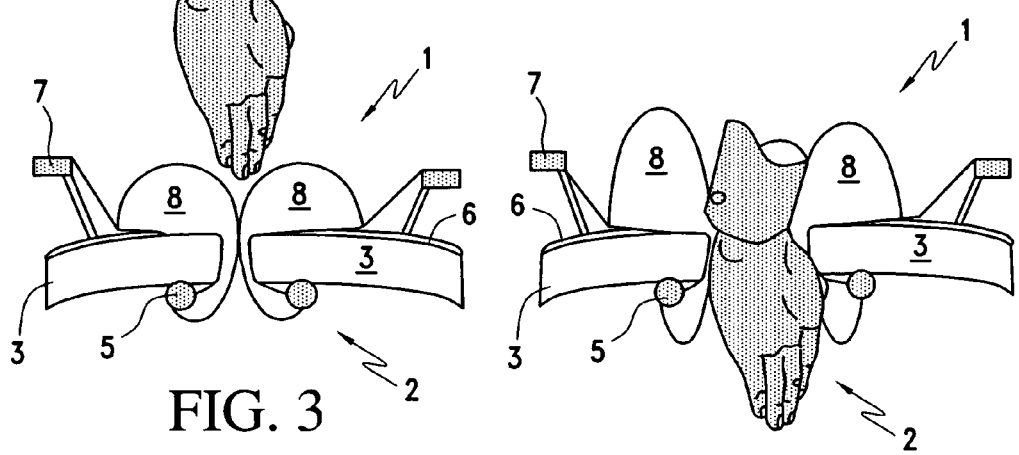
FIG. 3
FIG. 4

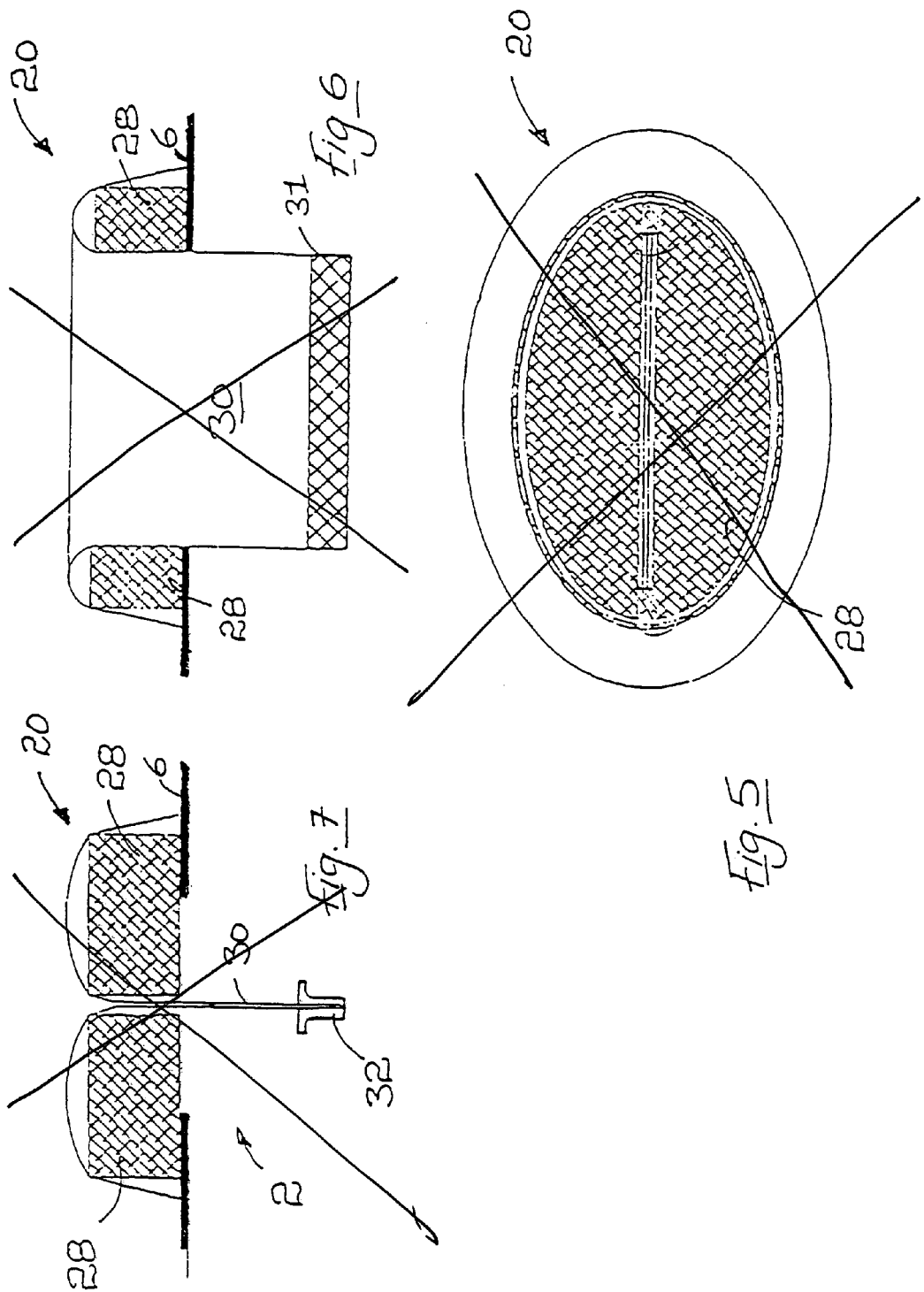

SURGICAL ACCESS DEVICE

BACKGROUND OF THE INVENTION

The present invention relates to a surgical device for use in minimally invasive surgery of the type using patient pneumoperitoneum and an access port.

SUMMARY OF THE INVENTION

Minimally invasive surgery of this type is carried out having introduced gas into a patient's body cavity through an incision and sealed the incision with an access port. The access port enables laproscopic and hand or instrument assisted surgery to be performed.

A sleeve forming such a port is shown in WO-A-95/07056 entitled "Apparatus for use in surgery". The access port sleeve shown is used to create a controlled pressurized environment within the sleeve while allowing a surgeon's arm to pass through the sleeve. During surgery, gas is pumped into the patient's body cavity where the surgery is to be performed and the sleeve prevents gas escaping while allowing the surgeon to operate using minimally invasive surgery techniques. The application shows a sleeve having a flange at a distal end provided with adhesive for adhering the device to a patient's body or alternatively a mounting ring to surround the incision in a patient's body. While providing a suitable apparatus for performing such surgery the device described suffers from the principle disadvantage that in use, the sleeve protrudes upwardly from the patient and may interfere with the activities of the surgery team. Additionally, the sleeve must be sealed against the surgeon's upper forearm by clamping the device to the arm sufficiently tightly to avoid gas leak around the area of the seal. This presents the surgeon with a problem both in sealing the sleeve and in subsequent mobility.

A further problem associated with the use of sleeves of the kind described is that a phenomenon known as "tenting" may occur. "Tenting" means that when the sleeve is adhered to the patient's skin or to a surgical drape and gas is induced into the patients abdominal cavity, there is a tendency for the sleeve to fill with gas and to pull away from the patient.

U.S. Pat. No. 5,366,478 discloses a sealing device for endoscopic surgical procedures. In one embodiment, the device has two inflatable toroidal sections connected by a transition section. The device is partially inserted into an abdominal opening in a deflated state, and then inflated to provide a seal for obstructing the passage of gas from the abdominal cavity during endoscopic surgery. Endoscopic instruments, or alternatively, the surgeon's hand, can penetrate through the lumen of the toroidal sections of the device. The lumen then conforms to the shape of the instrument or hand passed through it to maintain an adequate seal.

United Kingdom Patent Specification No. GB 2 275 420 discloses a medico-surgical system for access to a hollow viscus includes a member adapted to extend through an opening in the skin into the viscus of the patient so that one end of the member is located within the viscus and the other end terminates adjacent the skin. Balloons are provided for retaining the one end of the member within the viscus. The balloons also act as sealing means, adapted to seal the opening whilst allowing intermittent access to the viscus by means of a catheter.

U.S. Pat. No. 5,634,937 discloses a skin seal or trocar stabilizer with an inflatable balloon in the shape of a dumbbell, where the balloon may be stored within a cannula for easy placement in an incision and inflated to deploy the balloon inside the body, and a portion of the balloon expands inside the cannula, whereby medical instruments may be passed through the skin seal into a laparoscopic work space while the balloon is inflated, thereby allowing the use of normal short surgical instruments during laparoscopic procedures and during insufflation.

U.S. Pat. No. 5,636,645 discloses a method of performing surgery, which comprises making a first opening in a body cavity wall to permit entry of a surgeon's gloved hand. Next, the surgeon's gloved hand is placed into the body cavity through the opening and a gas is infused into the body cavity through the first opening or through the second opening. The surgical procedure is performed and the surgeon's hand is removed from the body cavity. The surgeon's gloved hand can be provided with a sealant for engaging the sides or surrounding tissue of the first opening, thereby creating a substantially gas-tight seal. The sealant can comprise an inflatable member circumferentially disposed around the forearm portion of the surgeon's glove or can comprise a disk having an adhesive on the distal surface for sealingly engaging the surrounding tissue of an opening in a body cavity wall.

U.S. Pat. No. 5,514,133 discloses an endoscopic surgical apparatus for enabling a surgeon to access directly the surgical site during an endoscopic procedure. This apparatus includes an opening extending longitudinally through the apparatus and being configured and dimensioned to receive a hand therethrough. A first plate engages against the outer surface of the abdominal wall. A second plate is spaced from the first plate and is movable between a first position and a second position wherein the second plate is in close cooperative alignment with the inner surface of the abdominal wall. An adjustment member is mounted to the second plate and actuates movement of the second plate between its first position and its second position. A first sealing member inhibits the flow of gas through said opening and is formed by a pair of overlapping seals. A flexible sleeve extends between the first and second plates and adjusts in length to accommodate various thicknesses of the abdominal wall. The sleeve also creates an access port for the passage of objects through the abdominal wall.

Accordingly, the present invention provides a surgical device for use in minimally invasive surgery of the type using an inflated body cavity accessible to a surgeon through an access port, defined by the device, surrounding an incision in a patient's body, the device having:— body cavity engagement means for insertion into the incision to locate the device in position;

fixing means for attaching the device to a patients skin; characterized in that the fixing means including a ring; characterized in that the body cavity engagement means is adjustable by the positioning of the ring; and the positioning of the ring retracting the body cavity engagement means to define an access port and create a sealing means between the incision and the body cavity engagement means;

the ring having an associated connector ring for receiving additional seals or medical instruments; and additional sealing means incorporating a foam shell to prevent substantial leakage of gas from the body cavity on inflation when in an inoperative position and formed to mould about a substantial portion of a surgeon's hand or surgical instrument on insertion in an operating position.

Preferably, the ring is an anchor ring formed for insertion into the incision.

Ideally, the sealing means is provided by a toroid cell formed to engage the incision between the fixing means and the body cavity engagement means.

Preferably, the cell forms a bladder through which the surgeon may access the body cavity, the bladder being filled with a viscous or semi-viscous liquid.

Preferably, the bladder is filled with saline, gel or foam.

The foam shell may be formed in two parts, or as a single part partially divided along one axis, the parts being movable relatively to allow a surgeon access to the body cavity.

In one arrangement the foam shell is formed by a plurality of individually disengageable layers. In this way the surgeon can adjust the height of the foam shell in response to particular needs by adding or removing foam layers. Thus a single device may be used on abdomens of varying thickness, enhancing flexibility of application. Furthermore, the rigidity created by the induced gas and foam apron allows for hand insertion and withdrawal without the aid of an assistant or requiring the surgeon to use the other hand. Additionally, the external valve created by the inclusion of a foam shell is enhanced by the pressure of the induced gas passing up between the double walled tube and acting to force the opposing faces of film together outside the patients abdominal cavity.

Preferably, the sealing means further incorporates a distal valve for insertion into the body cavity.

BRIEF DESCRIPTION OF THE DRAWINGS

Ideally, the distal valve includes a mechanical seal.

The invention will now be described more particularly with reference to the accompanying drawings, which show, by way of example only, various embodiments of a surgical device in accordance with the invention, in which:—

FIG. 1 is a top view of a surgical device in accordance with the invention;

FIG. 2 is a sectional view of the surgical device of FIG. 1 in the direction of the arrows A—A;

FIG. 3 is a sectional view similar to that shown in FIG. 2 showing the device in an inoperative position with a surgeon's hand approaching;

FIG. 4 is a sectional view as shown in FIGS. 2 and 3 showing the device in an operating position with the surgeons hand in place;

DETAILED DESCRIPTION OF THE PREFERRED EMBODIMENT

Figure 5:
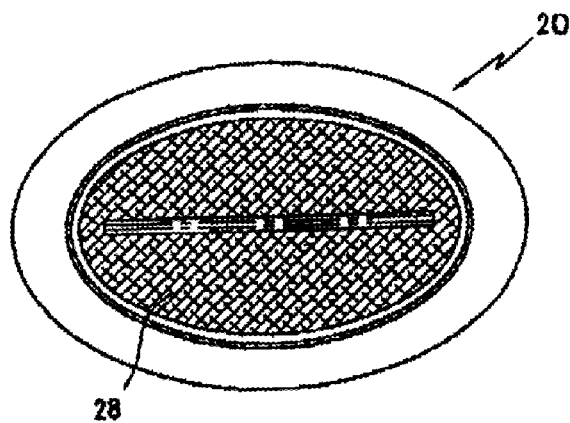
FIG. 5 is a plan view of and alternative surgical device in accordance with the invention.

Referring to the drawings, and initially to FIGS. 1 to 4, there is illustrated a surgical device according to the invention, indicated generally by the reference numeral 1. The surgical device 1 is formed for use in minimally invasive surgery of the type using an inflated body cavity indicated generally by the reference numeral 2. The cavity 2 is accessible to a surgeon through an access port, defined by the device 1, surrounding an incision in a patient's abdominal wall 3.

In more detail, the device 1 has a body cavity engagement means provided by an anchor ring 5 for insertion into the incision to locate the device 1 in position. The device 1 is held in position on the patient's skin out side the body by a fixing means provided in this case by an adhesive web 6. The ring 5 and web 6 ensure that the device 1 is securely fixed in position and surround the incision. It will be noted that the web may be replaced by any functional equivalent to secure the device in position.

The web 6 has an associated connector ring 7 for receiving additional seals to prevent loss of pressure from the cavity 2. The connector ring 7 may also be used for holding or guiding medical instruments into position over or in the incision.

The device 1 has a sealing means, provided in this embodiment of the invention, by a saline filled toroid cell 8 connected between the anchor ring 5 and the web 6. The cell 8 is formed to prevent substantial leakage of gas from the body cavity 2 on inflation when in an inoperative position see FIGS. 2 and 3. The cell 8 is also formed to mould to a substantial portion of a surgeon's hand or surgical instrument when in an operating position (see FIG. 4). The cell 8 is also formed to allow for the removal of operative tissue when in an operating position with or without pneumoperitoneum established.

It will be noted that the cell may be filled with any suitable material and represents a significant improvement over prior art devices, which are inflated with air. The use of a liquid such as a sealed saline bladder improves hygiene around the wound and responds more quickly to a movement by a surgeon's hand. Additionally the invention overcomes problems associated with inflatable bladders, which will leak air if under inflated or be overly restrictive to movement if over inflated.

It will further be noted that the sealing means is described as a toroid or donut shaped cell, but that it could be equally provided as a lip shaped or elliptical cell tapering slightly at either end.

In use, an incision is made in the abdominal wall 3 and the anchor ring 5 passed through the incision into the cavity 2. The anchor ring 5 is moved when in the cavity 2 such that the ring 5 surrounds the incision. The web 6 is then attached to the patients skin to fix the device 1 in position with the cell 8 being connected between the web 6 and the ring 5 and engaging the portions of the abdominal wall 3 exposed by the incision. The cell 8 seal the incision and the abdominal cavity 2 may be inflated as required by the surgeon to an inoperative position FIG. 2. The surgeon can gain access to the cavity 2 losing a minimum of gas pressure by passing a hand or instrument through the center of the toroid or donut shaped cell 8. When the hand or instrument is in the operating position (FIG. 4) the cell moulds to the hand or instrument to prevent loss of pressure.

Figure 6:
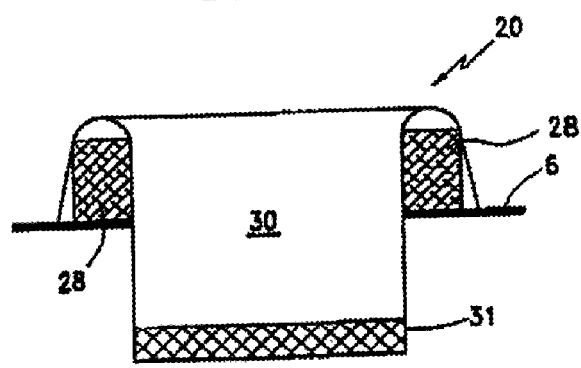
FIG. 6 is a front view of the surgical device of FIG. 5.
Figure 7:
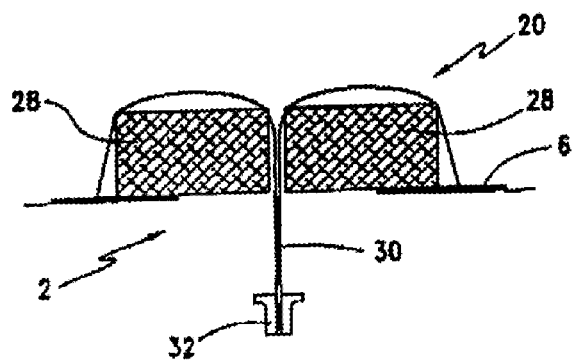
FIG. 7 is an end view of the surgical device of FIGS. 5 and 6.

Referring now to FIGS. 5 to 7 there is illustrated a further surgical device in accordance with the invention indicated generally by the reference numeral 20, in which parts similar to those identified with reference to FIGS. 1 to 4 are identified by the same reference numerals generally. In this embodiment the sealing means is in two sections. A foam shell 28 is in this case formed in two parts to envelop the incision site. It will be understood that the foam shell may equally be provided as a single part, divided or split along an axis. The parts of the shell 28 are movable relatively to allow a surgeon access to the body cavity and can be biased together to seal the cavity 2 when not in use. A sleeve 30 connected to the web 6 covers the shell 28 and passes into the cavity 2 and is terminated in the cavity 2 by a distal valve 31 having a mechanical seal 32. It will also be understood that the web 6 may equally be provided by an anchoring ring.

In use, the parts of the foam shell 28 are separated as before by the surgeon's hand or instrument and the foam moulds the shape of the inserted object to prevent loss of pressure. The inserted object then travels through the sleeve 30 to the distal valve 31 inside the cavity 2 and opens the mechanical seal 32. When the task has been completed the inserted object is removed and the mechanical seal 32 being so biased closes. The pressure in the cavity 2 is such during procedures of this type to close the sleeve 30 along its length as the object is removed and a final seal is provided by the foam shell 28 decompressing when the object has been removed.

The use of a foam shell has a number of advantages over known systems. For example, trauma at the incision is minimised as shock associated with downward pressure when inserting the surgeon's hand is largely absorbed by the foam. Tenting is eliminated as the foam shell reduces the volume of gas in the proximal end of the sleeve. The foam may also be used to absorb liquids such as blood in a hygienic manner and may reduce the effect of blood and body fluids on the anchoring ring. Furthermore it is envisaged that the lifting action of the foam may be used to retract tissue or for creating additional anchoring forces or between the distal valve and the abdominal wall. The cell may also be formed in any suitable manner to allow for the removal of operative tissue during the course of an operation whether or not pneumoperitoneum has been established.

It will be noted that the sleeve and valve may incorporate means for preventing the sleeve returning through the incision accidentally. These means may include but are not limited to an angled flap or flaps on the distal valve, tensioning means in the sleeve such as weld lines or a physical connection to a body part including the abdominal wall.

It will be understood that the foam shell may also be provided as a single block, defining a passageway therein, to allow communication between the exterior and the cavity.

It will of course be understood that the invention is not limited to the specific details described herein, which are given by way of example only, and that various modifications and alterations are possible within the scope of the invention as defined in the appended claims.

The invention claimed is:

1. A surgical device for use in minimally invasive surgery of the type using an inflated body cavity accessible to a surgeon through an access port, defined by the device, surrounding an incision in a patient's body, the device having:
   body cavity engagement means for insertion into the incision to locate the device in position;
   fixing means for attaching the device to a patient's skin, the fixing means including a ring; wherein the body cavity engagement means is adjustable by the positioning of the ring so that the positioning of the ring retracts the body cavity engagement means to define an access port and creates a sealing means between the incision and the body cavity engagement means; and
   additional sealing means incorporating a toroid cell comprising a sealed, non-inflating bladder entirely filled with one of a liquid and a gel to prevent substantial leakage of gas from the body cavity on inflation of the body cavity when the sealing means is in an inoperative position and formed to mould about a substantial portion of a surgeon's hand or surgical instrument on insertion in an operating position.

* * * * *

UNITED STATES PATENT AND TRADEMARK OFFICE
CERTIFICATE OF CORRECTION

PATENT NO. : 7,214,185 B1 Page 1 of 2
APPLICATION NO. : 09/936840
DATED : May 8, 2007
INVENTOR(S) : Damien Rosney et al.

It is certified that error appears in the above-identified patent and that said Letters Patent is hereby corrected as shown below:

On the front page of the patent, the Assignee's name "Maclachlan & Donaldson" should be deleted, and in its place --Gaya Limited-- should be inserted.

The sheet of drawings consisting of figures 5-7 should be deleted to appear as per attached figures 5-7.

In line 2 of the Abstract "though" should be deleted, and in its place --through-- should be inserted.

In column 2, line 50, the term "patients" should be deleted, and in its place --patient's-- should be inserted.

In column 3, line 25, the term "patients" should be deleted, and in its place --patient's-- should be inserted.

In column 3, lines 45-46, the term "surgeons" should be deleted, and in its place --surgeon's-- should be inserted.

In column 3, line 47, the term "and" should be deleted, and in its place --an-- should be inserted.

In column 4, line 16, directly after the term "position" a --,-- should be inserted.

Signed and Sealed this

Twenty-first Day of July, 2009

JOHN DOLL
*Acting Director of the United States Patent and Trademark Office*